(12) United States Patent
Shin et al.

(10) Patent No.: US 10,485,659 B2
(45) Date of Patent: Nov. 26, 2019

(54) PROSTHETIC HEART VALVE USING PERICARDIUM AND METHOD FOR MANUFACTURING SAME

(71) Applicants: TAEWOONG MEDICAL CO., LTD., Gyeonggi-do (KR); Kyong Min Shin, Gyeonggi-do (KR)

(72) Inventors: Kyong Min Shin, Gyeonggi-do (KR); Kang Sun Hong, Gyeonggi-do (KR)

(73) Assignees: TAEWOONG MEDICAL CO., LTD., Gyeonggi-do (KR); Kyong Min Shin, Gyeonggi-do (KR)

( * ) Notice: Subject to any disclaimer, the term of this patent is extended or adjusted under 35 U.S.C. 154(b) by 0 days.

(21) Appl. No.: 15/551,214

(22) PCT Filed: Sep. 8, 2015

(86) PCT No.: PCT/KR2015/009439
§ 371 (c)(1),
(2) Date: Aug. 15, 2017

(87) PCT Pub. No.: WO2016/171340
PCT Pub. Date: Oct. 27, 2016

(65) Prior Publication Data
US 2018/0036120 A1    Feb. 8, 2018

(30) Foreign Application Priority Data

Apr. 22, 2015  (KR) .................. 10-2015-0056661

(51) Int. Cl.
*A61F 2/24*    (2006.01)
*A61L 27/36*   (2006.01)
(Continued)

(52) U.S. Cl.
CPC .............. *A61F 2/2412* (2013.01); *A61F 2/24* (2013.01); *A61F 2/2415* (2013.01);
(Continued)

(58) Field of Classification Search
CPC .... A61F 2/2415; A61F 2/2412; A61F 2/2427; A61F 2/2418; A61F 2210/0014;
(Continued)

(56) References Cited

U.S. PATENT DOCUMENTS 6,454,799 B1 *  9/2002  Schreck ................ A61F 2/2418
                                                     623/2.18
7,101,396 B2 *  9/2006  Artof .................... A61F 2/2418
                                                     623/2.14
(Continued)

FOREIGN PATENT DOCUMENTS

KR    1020020082217    10/2002
KR    1020080103510    11/2008
(Continued)

*Primary Examiner* — Paul B Prebilic
(74) *Attorney, Agent, or Firm* — IP & T Group LLP

(57) ABSTRACT

A prosthetic heart valve using a pericardium is disclosed where: three hetero-biological tissue slices, which are extracted in a quadrangular shape from a bovine pericardium or a porcine pericardium, are prepared; each hetero-biological tissue slice is folded so as to form an inner tissue slice inside and an outer tissue slice outside, the outer tissue slice being longer than the inner tissue slice; each of the inner tissue slice and outer tissue slice is coupled by sewing in a semicircular shape with a first coupling thread such that each inner tissue slice forms a pulmonic valve slice inside the first coupling thread and a fixing slice outside the first coupling thread such that each hetero-biological tissue slice is formed in a cylindrical shape by allowing each slice to be adjacent to each other. The disclosed prosthetic heart valve has increased durability and prevents reverse blood flow.

14 Claims, 13 Drawing Sheets

(51) Int. Cl.
*A61F 2/90* (2013.01)
*A61F 2/95* (2013.01)

(52) U.S. Cl.
CPC .......... *A61F 2/2418* (2013.01); *A61F 2/2427* (2013.01); *A61L 27/36* (2013.01); *A61F 2/90* (2013.01); *A61F 2002/9522* (2013.01); *A61F 2210/0076* (2013.01); *A61F 2220/0075* (2013.01); *A61F 2230/0019* (2013.01); *A61F 2230/0078* (2013.01); *A61F 2250/0037* (2013.01); *A61F 2250/0039* (2013.01)

(58) Field of Classification Search
CPC ...... A61F 2210/0076; A61F 2220/0075; A61F 2230/0069; A61F 2240/001; A61L 27/36; A61L 2400/16; A61L 2430/20; A61L 2430/22
See application file for complete search history.

(56) References Cited

U.S. PATENT DOCUMENTS

| | | | |
|---|---|---|---|
| 7,261,732 | B2 | 8/2007 | Justino |
| 8,109,995 | B2 | 2/2012 | Paniagua et al. |
| 8,308,797 | B2 * | 11/2012 | Paniagua .............. A61F 2/2412 623/2.14 |
| 2003/0114913 | A1 * | 6/2003 | Spenser ................ A61F 2/2412 623/1.11 |
| 2010/0023120 | A1 * | 1/2010 | Holecek ................ A61F 2/2412 623/2.19 |
| 2012/0010697 | A1 * | 1/2012 | Shin ...................... A61F 2/2415 623/1.26 |
| 2012/0083879 | A1 * | 4/2012 | Eberhardt ............ H01M 4/131 623/2.18 |

FOREIGN PATENT DOCUMENTS

| | | |
|---|---|---|
| KR | 1020120004677 | 1/2012 |
| KR | 101241268 | 3/2013 |

* cited by examiner

FIG. 11A
FIG. 11B
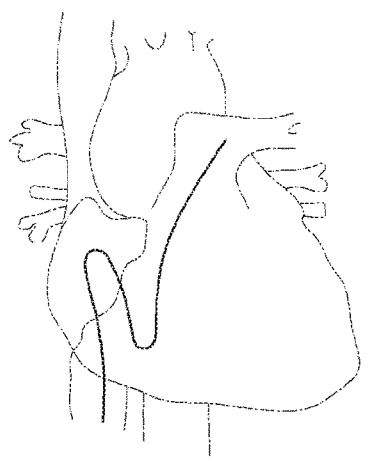
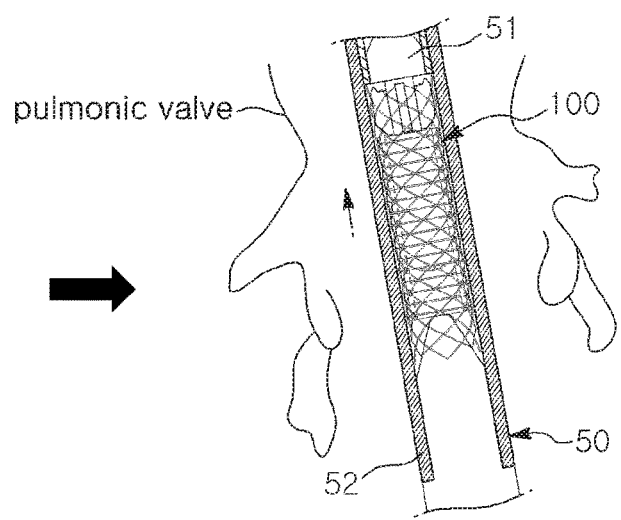
FIG. 11D
FIG. 11C
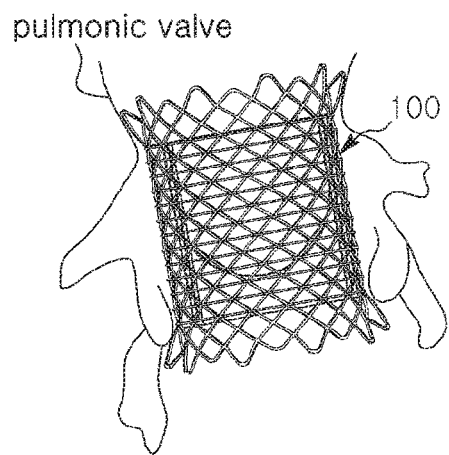
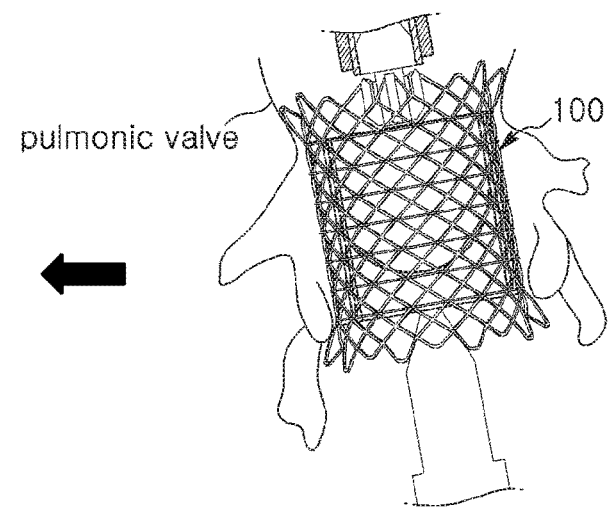

aortic valve, pulmonic valve

PROSTHETIC HEART VALVE USING PERICARDIUM AND METHOD FOR MANUFACTURING SAME This application is a national stage application of PCT/KR2015/009439 filed on Sep. 8, 2015, which claims priority of Korean patent application number 10-2015-0056661 filed on Apr. 22, 2015. The disclosure of each of the foregoing applications is incorporated herein by reference in its entirety.

TECHNICAL FIELD

The present invention relates to a prosthetic heart valve and, more particularly, to a prosthetic heart valve using pericardium and a method for manufacturing the same, whereby the prosthetic heart valve utilizes heterogeneous tissue pieces that have been extracted in a quadrangular shape from a bovine pericardium or a porcine pericardium, folded in half to both perform the function of a valve and perform a securing function of securing to a wire stent; prevents the valve conduit at the wire stent from being ruptured by prolonged use or by the pressure of the blood flow; and prevents reverse blood flow.

BACKGROUND ART

Generally, a prosthetic heart valve is used as a surgical replacement for a person's heart valve if it is damaged or has a functional deficiency. It is also used to prevent reverse blood flow in recently developed prosthetic hearts or ventricular assist devices.

Prosthetic heart valves may be divided into mechanical valves, tissue valves, and polymer valves according to the main material used, where a mechanical valve uses a circular or semicircular hinge flap with its movement restricted to one direction to prevent reverse blood flow, and a tissue valve includes the heart valve or the pericardium surrounding the heart of an animal fabricated into a structure similar to that of the aortic valve or pulmonic valve of the heart. A polymer valve uses medical-grade polymers that are molded into a form similar to the aortic valve or are fabricated into a structure that serves as a unidirectional check valve.

Here, the structure of an aortic valve or a pulmonic valve includes three flexible membranes for preventing reverse blood flow, and hence is referred to as a trilobate valve, and existing tissue valves and polymer valves are usually fabricated in a form similar to this.

Furthermore, since the leaflets of a prosthetic heart valve must possess a flexible quality similar to the leaflets of a biological heart valve and must operate within the body for an extended period of time without irregularity, durability is an important criterion in selecting the material. Also, since there is direct contact with blood, a material having good compatibility with blood must be chosen or a material that has been imbued with compatibility with blood must be used.

The existing method of manufacturing such a trilobate polymer valve includes two steps. First, the part corresponding to the leaflets is first fabricated.

This process entails fabricating molds having a form similar to that of the leaflets, repeating the processes of immersing the molds into a polymer solution and drying, and separating the polymer membranes from the molds to form leaflet shapes. Next, a valve conduit for surrounding the fabricated leaflets may have three leaflets attached therein to complete the process. Here, it is advantageous to form a sinus for each leaflet within the valve conduit in order to minimize regions where the blood remains stagnant when the valve is closed, the thickness may be two to twenty times thicker compared to the leaflets when considering the thickness of the aorta within the body, and the strength should be of a level that is sufficient for use within the body.

The existing process of manufacturing a trilobate polymer valve such as that described above requires providing the polymer in a solution state and fabricating the valve conduit separately by injection molding or a different method before attaching the components. The time required for production was several days, the level of quality was not consistent due to the manual labor involved in the immersing and attaching processes, and the usefulness was low because of the low productivity.

As an effort to resolve these problems, the stent valve of Patent Document 1 was proposed.

The stent valve according to the related art mentioned above includes: (a) a single radial expanding vessel stent that has a diameter, a proximal end, and a distal end; and (b) a valve that has a valve proximal end and a valve distal end, is at least partially positioned inside the stent, and forms a valve opening by means of the valve proximal end being arranged at the proximal end of the stent, wherein the valve includes at least two pocket structures for blocking the flow of blood, the pocket structures are positioned within the stent, the pocket structures include flexible portions that cooperate to form a valve opening adjacent to the proximal end of the stent, the flexible portions include outer portions that connect to the stent and extend inwards from the stent to form the valve opening, each of the pocket structures includes a layer that extends from the apex of the pocket structure to towards the proximal end of the stent, the layer is sutured to the inside of the stent to cover the inside, and the apex of the pocket structure is positioned adjacent to the distal end of the stent.

However, the stent valve according to the related art described above, where two pocket structures are inserted into and connected within the vessel stent to perform the function of a valve and operate such that blood may flow towards the heart but may not move out of the heart, is vulnerable to the problem of tearing due to prolonged use at the portion where the vessel stent and the pocket structures are connected as well as the problem of the valve losing its functionality when the elasticity of the pocket structures is lost.

Also proposed were the stent-valve for valve replacement and associated methods and systems for surgery of Patent Document 2.

The valve according to the related art mentioned above includes a valve component; and a stent component that includes a first section, a second section for housing the valve component, and a third section, where the first section includes an annular groove.

However, the valve according to the related art described above is manufactured in the form of an integrated body, so that not only may the manufacturing procedure be complicated and the manufacturing costs be increased, but also tearing may occur at the connecting portions when it is used coupled to a wire stent.

Also proposed was the cardiac valve prosthesis for replacement of the aortic valve of Patent Document 3.

The valve according to the related art mentioned above is made from a bovine pericardium and is formed by an inner sheet having three semicircular portions and an outer sheet made from the bovine pericardium, with the inner sheet and the outer sheet sutured together, rolled into a cylindrical shape, and sutured at both ends.

However, the valve according to the related art described above entails the problem of tearing occurring at the connecting portions when it is used coupled to a separate wire stent.

Also proposed was the prosthetic heart valve of Patent Document 4.

The valve according to the related art mentioned above includes a plurality of thin, flexible leaflets, each of the leaflets having an inner face, an outer face, an inflow edge, an out-flow edge, and side edges, the plurality of leaflets being sewn together along at least a portion of their side edges so as to form a substantially tubular valve structure having an in-flow end and an out-flow end, adjacent leaflets being arranged so that their side edges are substantially aligned and the inner faces of the leaflets engage each other adjacent the side edges, whereby the valve structure is movable between a closed position in which the out-flow edges of adjacent leaflets engage each other, and an open position in which the out-flow edges of adjacent leaflets are separated from each other except along the side edges, and the sewn portions of the side edges of the leaflets bias the leaflets toward a partially closed position.

However, with the valve according to the related art described above, the sewing required for the manufacture of the cylindrical shape results in the sewn portions protruding outwards, which may leave gaps between the sewn portions and the inner cavity of an artery during a surgical procedure or may make connection difficult when the valve is used coupled with a separate wire stent.

DISCLOSURE

Technical Problem

Accordingly, the present invention has been made keeping in mind the above problems occurring in the related art, and an objective of the present invention is to provide a prosthetic heart valve using pericardium and a method for manufacturing the same, where the prosthetic heart valve may utilize heterogeneous tissue pieces, which have been extracted in a quadrangular shape from a bovine pericardium or a porcine pericardium, folded in half to simultaneously perform the function of a valve and perform a securing function of securing to a wire stent, prevent the valve conduit at the wire stent from being ruptured by prolonged use or by the pressure of the blood flow, and prevent reverse blood flow.

Technical Solution

In order to accomplish the objective above, the present invention provides a method for manufacturing a prosthetic heart valve using a pericardium, as well as the manufactured prosthetic heart valve. The method includes: preparing three heterogeneous tissue pieces, the heterogeneous tissue pieces extracted in a quadrangular shape from a bovine pericardium or a porcine pericardium; folding each of the heterogeneous tissue pieces to form an inside tissue piece on the inside and an outside tissue piece on the outside, the outside tissue piece having a greater length than the inside tissue piece; connecting respectively the inside and outside tissue pieces by sewing with a first connecting thread along a semicircular shape having one side open such that each of the inside tissue pieces has a valve piece formed on the inside of the first connecting thread and a securing piece formed on the outside of the first connecting thread; arranging the heterogeneous tissue pieces next to one another to form a cylindrical form; placing both ends of the heterogeneous tissue pieces in contact with one another and exposing outward to connect the heterogeneous tissue pieces by sewing with a second connecting thread along a vertical direction; folding the heterogeneous tissue pieces at both ends to complete a valve conduit having folded portions; preparing a wire stent by intertwining wires made of an superelastic shape-memory alloy along the circumferential direction and the lengthwise direction of a cylinder in a network form, the wire stent comprising a cylindrical body having a plurality of spaces formed therein and expanding portions expanding outward from both sides of the cylindrical body; and inserting the valve conduit into the inside of the wire stent and connecting the spaces and the outside tissue pieces and the securing pieces by sewing with a third connecting thread along a horizontal direction to complete a valve conduit stent, whereby the valve conduit stent is compressed by a commonly used crimper and latched onto a hook portion of a catheter and is inserted into an outer tube of the catheter by a movement of the hook portion.

Advantageous Effects

With an embodiment of the present invention, the first, second, and third connecting threads are sewed repeatedly in a '∞' shape, so that the valve conduit secured to the wire stent may withstand the pressure of the blood flow for extended periods of time.

With an embodiment of the present invention, the second connecting threads are sewed including the ends of the first connecting threads, so that the valve pieces may withstand the pressure of the blood flow for extended periods of time.

With an embodiment of the present invention, the ends of the heterogeneous tissue pieces that are exposed to the exterior in contact with one another are connected by sewing with the second connecting threads along vertical directions, so that the gaps between the ends of the heterogeneous tissue pieces may be made narrower.

Also, an embodiment of the present invention has each heterogeneous tissue piece folded into folded portions at both ends, so that the gaps between the ends of the heterogeneous tissue pieces may be further narrowed.

Moreover, according to an embodiment of the present invention, the second connecting threads and the folded portions prevent the gaps between the ends of the heterogeneous tissue pieces from becoming opened by reverse blood flow, so that the valve pieces may maintain functioning as a valve.

Since, in an embodiment of the present invention, the folded portions are positioned in 120° intervals, the valve conduit secured to the wire stent may withstand the pressure of the blood flow for extended periods with uniform supportive forces.

Also, with an embodiment of the present invention, the uniform supportive forces allow the shapes of the valve pieces to be deformed in the same manner by the pressure of the blood flow.

An embodiment of the present invention has the length of the outside tissue pieces formed equal to the length of the cylindrical body, making it easier to adjust the position of the valve conduit within the wire stent.

An embodiment of the present invention has the spaces of the wire stent and the outside tissue pieces and securing pieces connected by sewing with third connecting threads along a horizontal direction, so that the valve conduit may evenly withstand the pressure of the blood flow.

An embodiment of the present invention uses latching folded ends that are formed longer than non-latching folded ends, so that the latching folded ends of the valve conduit stent compressed by a commonly used crimper can be readily latched onto the hook of the hook portion.

Since the hook is formed in the shape of an isosceles triangle according to an embodiment of the present invention, the time required for the latching folded ends of the valve conduit stent to be latched onto or be released from the hook can be reduced.

Also, according to an embodiment of the present invention, the edge of the hook is rounded, so that the latching folded ends of the valve conduit stent may readily move along the hook.

Further, an embodiment of the present invention has the mount surface formed horizontally, so that the latching folded ends of the valve conduit stent are not embedded as deeply as in the related art.

In other words, according to an embodiment of the present invention, the latching folded ends of a compressed valve conduit stent may evenly expand simultaneously at the hook, allowing the user to position the valve conduit stent at the desired operating position.

That is, an embodiment of the present invention can prevent the problem found in the related art concerning the difficulty in releasing the latching folded ends of the valve conduit stent from the hook when they are embedded too deeply behind the hook.

Also, an embodiment of the present invention prevents the problem found in the related art of a part of the latching folded end of an expanded valve conduit stent being caught on the hook at the operating position and causing the surgical procedure to remain in an unstable state.

Furthermore, an embodiment of the present invention prevents the problem of the valve conduit stent moving from the operating position as occurs in the related art when the hook portion connected to the inner tube of the catheter must be moved several times to release the latching of the latching folded end from the hook.

Moreover, an embodiment of the present invention prevents the problem of further movement from the operating position desired by the user as occurs in the related art when, as a result of the method above, the latching onto the hook is finally released and a part of the latching folded end expands and applies elastic force.

Thus, an embodiment of the present invention utilizes heterogeneous tissue pieces, which have been extracted in a quadrangular shape from a bovine pericardium or a porcine pericardium, folded in half to provide the advantages of simultaneously performing the function of a valve and performing a securing function of securing to a wire stent, preventing the valve conduit at the wire stent from being ruptured by prolonged use or by the pressure of the blood flow, and preventing reverse blood flow.

DESCRIPTION OF DRAWINGS

FIGS. 1A to 3B show diagrams illustrating a process of manufacturing a valve conduit by sewing heterogeneous tissue pieces with first and second connecting threads according to an embodiment of the present invention.

FIGS. 9A to 11D show diagrams illustrating a process of applying a prosthetic heart valve according to an embodiment of the present invention through a femoral artery or a femoral vein of the leg to an aortic valve or a pulmonic valve of the heart in a surgical procedure.

BEST MODE

Figure 1A:
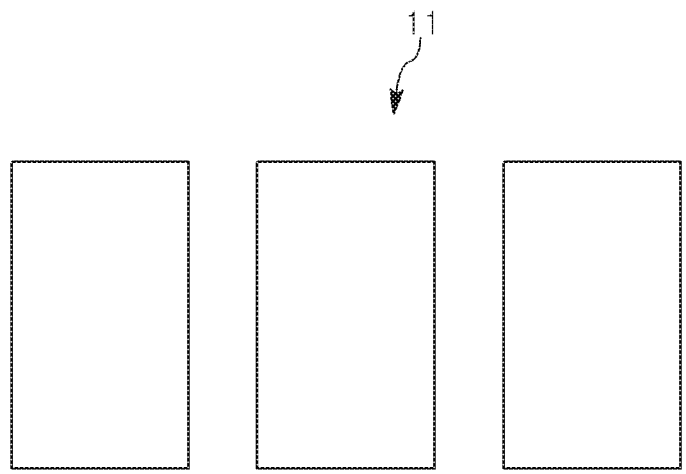
Figure 1A:
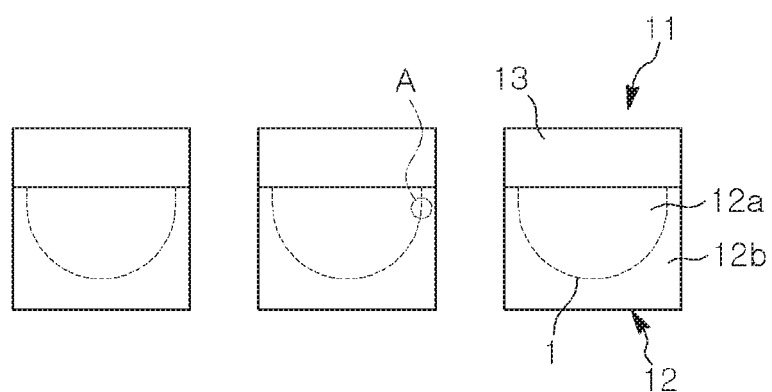
Figure 1A:
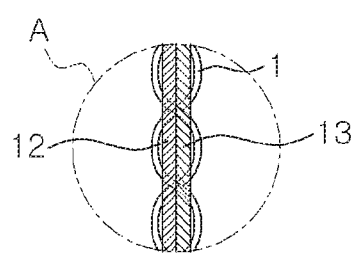
Figure 2A:
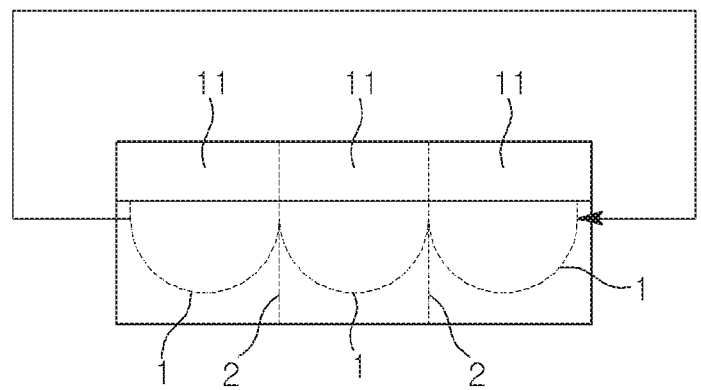
Figure 2A:
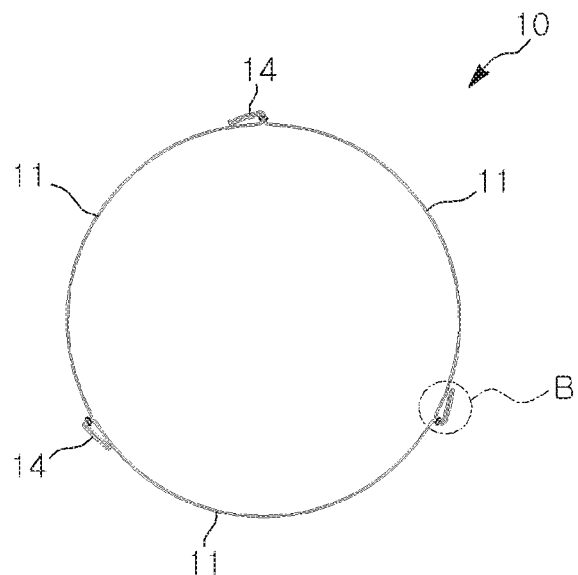
Figure 2A:
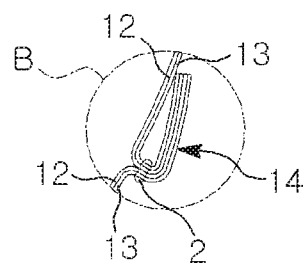
Figure 3A:
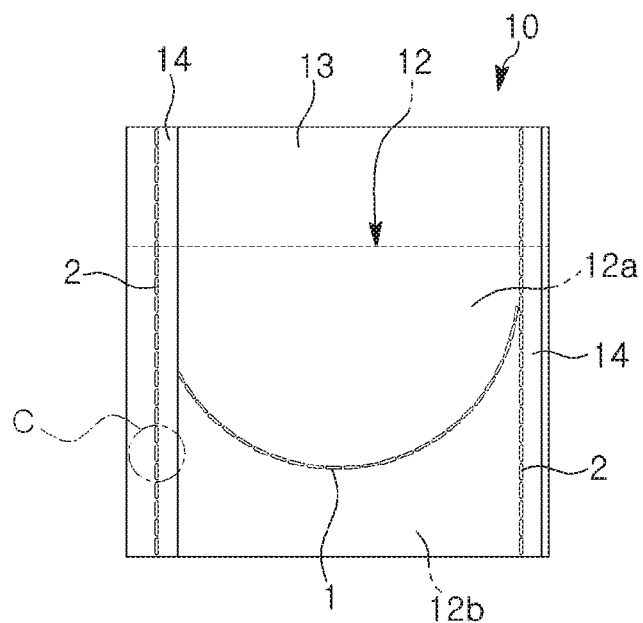
Figure 3B:
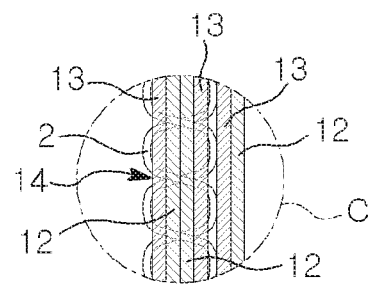

Preferred embodiments of the present invention set forth above are described below in more detail with reference to the accompanying drawings.

A process for manufacturing a prosthetic heart valve 100 using a pericardium according to an embodiment of the present invention first includes preparing three heterogeneous tissue pieces 11 that have been extracted in a quadrangular shape from a bovine pericardium or a porcine pericardium, as illustrated in FIGS. 1A to 3B.

Then, each of the heterogeneous tissue pieces 11 is folded in half such that an inside tissue piece 12 is formed on the inside and an outside tissue piece 13 that is longer than the inside tissue piece 12 is formed on the outside.

Next, for each piece, the inside and outside tissue pieces 12, 13 are connected by sewing with a first connecting thread 1 in a semicircular shape having one side open, such that the inside tissue piece 12 forms a valve piece 12a on the inside of the first connecting thread 1 and a securing piece 12b on the outside of the first connecting thread 1. Here, the first connecting threads 1 are sewed in a repeated '∞' shape.

The heterogeneous tissue pieces 11 are arranged next to one another to form a cylindrical form, the ends of the heterogeneous tissue pieces 11 are placed in contact with one another, exposed outward, and connected by sewing with second connecting threads 2 along a vertical direction.

Here, the second connecting thread 2 sews across the ends of the first connecting threads 1, which are each sewn in a semicircular shape with one side open. Also, the second connecting threads 2 are sewed in a repeated '∞' shape.

Next, the ends of the heterogeneous tissue pieces 11 are folded about the second connecting threads 2 to form folded portions 14, thus completing a valve conduit 10.

Figure 4A:
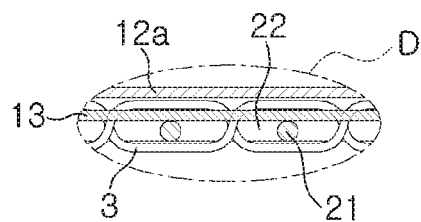
FIGS. 4A and 5 show diagrams illustrating a process of manufacturing the valve conduit stent of a prosthetic heart valve by inserting the valve conduit into a wire stent and sewing with third connecting threads according to an embodiment of the present invention.
Figure 4B:
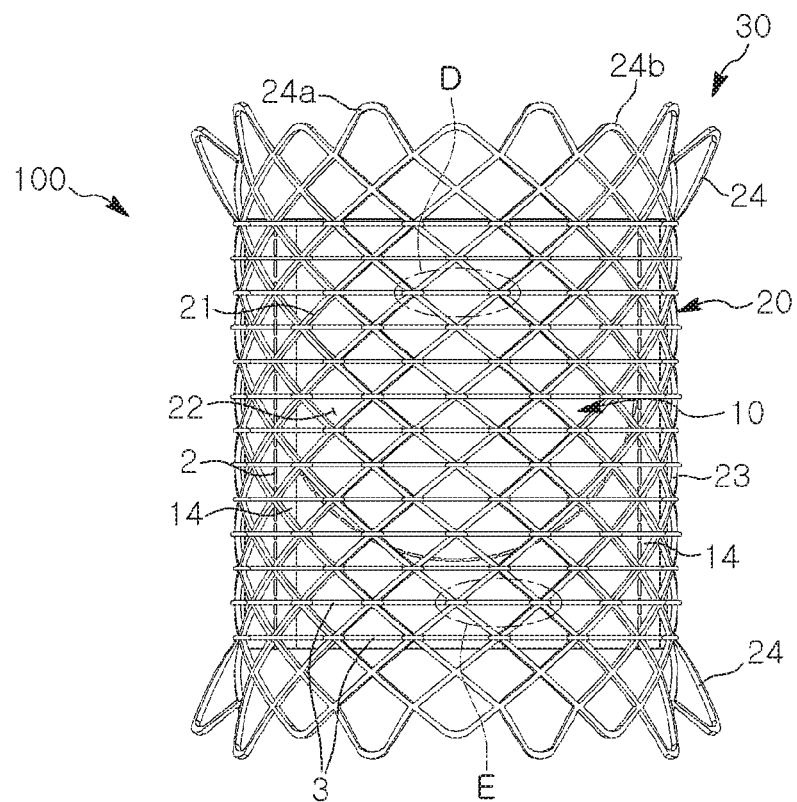
Figure 4C:
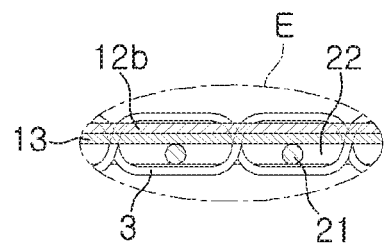
Figure 5:
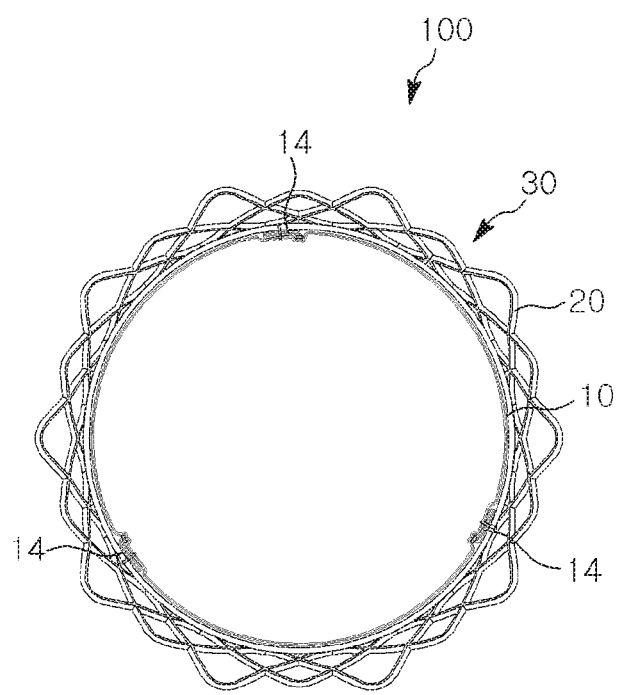

Also, as illustrated in FIGS. 4B and 5, a wire stent 20 is prepared, the stent including a cylindrical body 23, in which multiple spaces 22 are formed, and expanding portions 24, which are shaped as truncated cones and which expand outward from both ends of the cylindrical body 23, by intertwining wires 21 made of a superelastic shape-memory alloy along the circumferential direction and the lengthwise direction of a cylinder in a network form.

Here, an expanding portion 24 comprises latching folded ends 24a that have long protruding lengths and non-latching folded ends 24b that have protruding lengths shorter than the latching folded ends 24a.

That is, the non-latching folded ends 24b are formed in-between the neighboring latching folded ends 24a.

Also, the length of the cylindrical body 23 is made equal to the length of the outside tissue pieces 13.

Next, the valve conduit 10 is inserted inside the wire stent 20, after which the spaces 22, outside tissue pieces 13, and securing pieces 12b are connected by sewing with third connecting threads 3 along horizontal directions to complete a valve conduit stent 30.

That is, the third connecting threads 3 are sewed repeatedly in a '∞' shape, with the valve pieces 12a excluded. Also, the third connecting threads 3 are sewed in horizontal directions in predetermined intervals along the lengthwise direction of the cylindrical body 23.

More specifically, the third connecting threads 3 sew together and connect the spaces 22 and the outside tissue pieces 13, excluding the valve pieces 12a, at the upper part of the valve conduit stent 30 as seen from the front, and sew together and connect the spaces 22, the outside tissue pieces 13, and the securing pieces 12b at the lower part of the valve conduit stent 30 as seen from the front.

In this manner, the prosthetic heart valve 100 using a pericardium is manufactured.

Figure 6A:
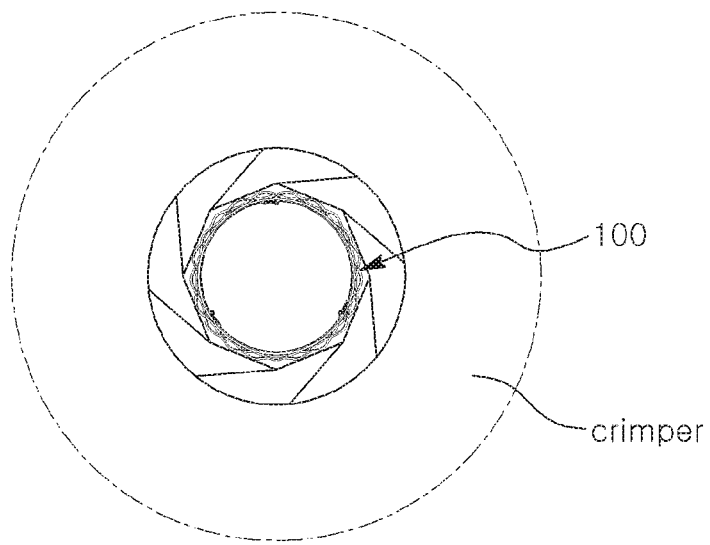
FIGS. 6A to 8D show diagrams illustrating a process of applying a prosthetic heart valve according to an embodiment of the present invention through a partially incised chest cavity to an aortic valve or a pulmonic valve of the heart in a surgical procedure.
Figure 6A:
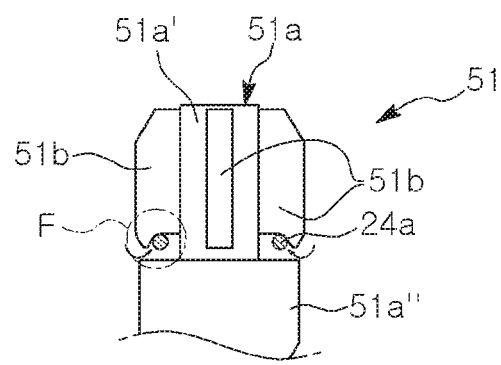
Figure 6A:
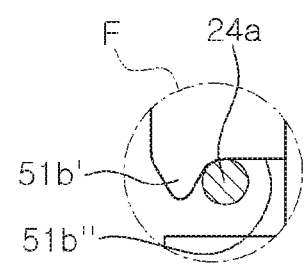
Figure 6C:
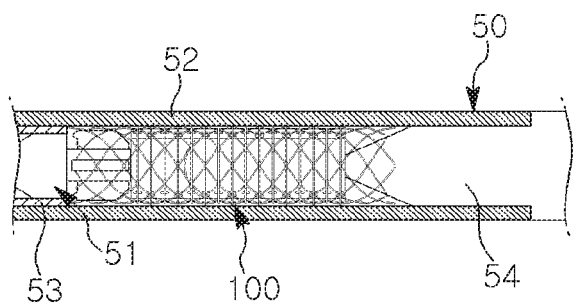
Figure 7A:
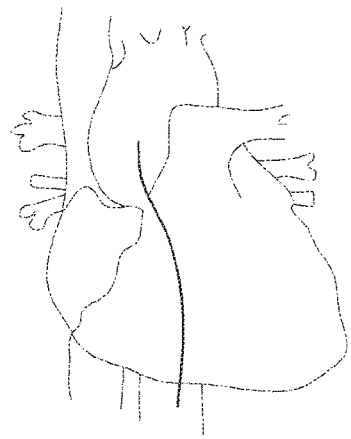
Figure 7B:
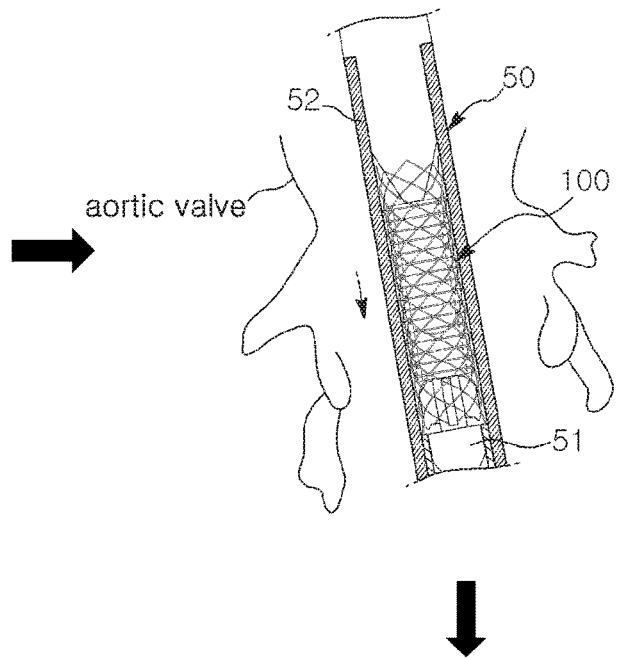
Figure 7D:
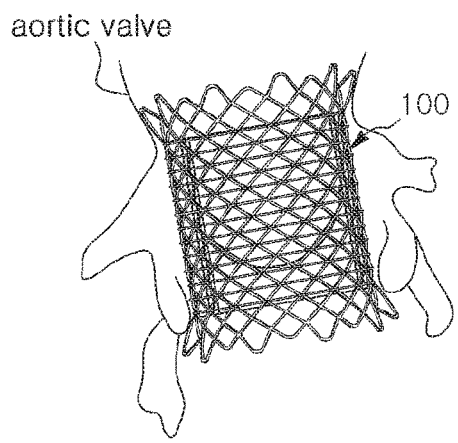
Figure 7C:
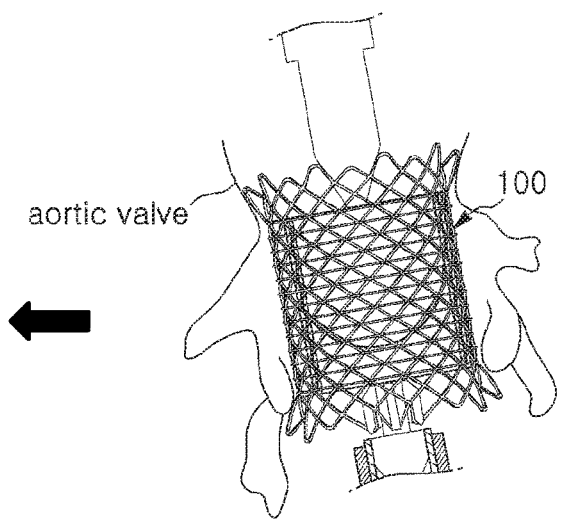
Figure 8A:
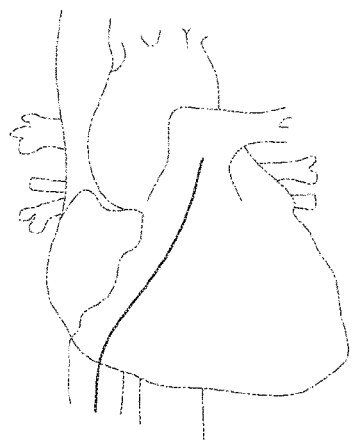
Figure 8B:
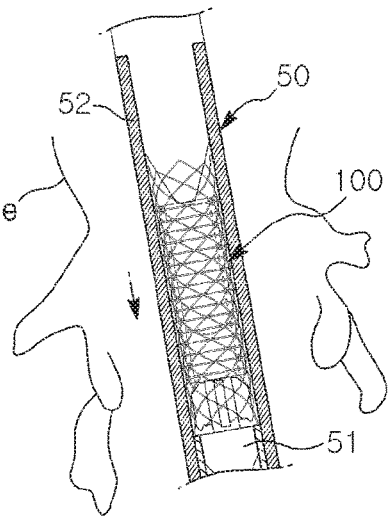
Figure 8D:
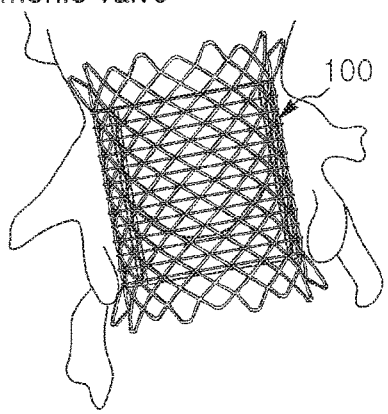
Figure 8C:
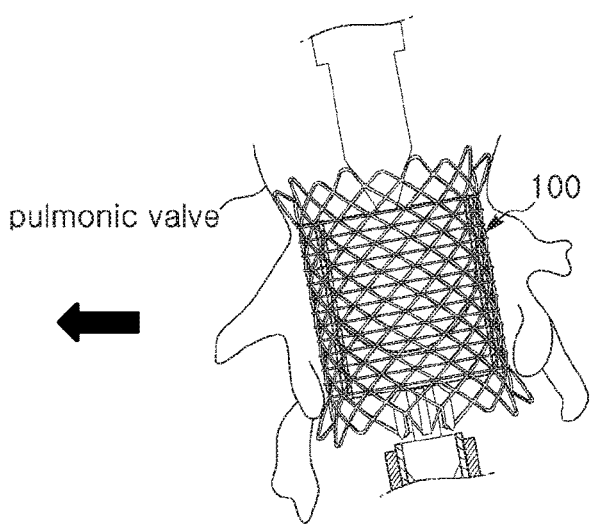
Figure 9A:
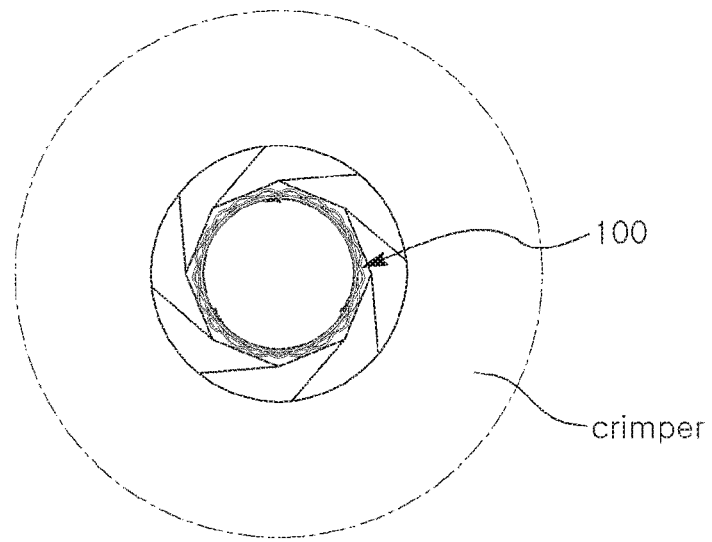
Figure 9A:
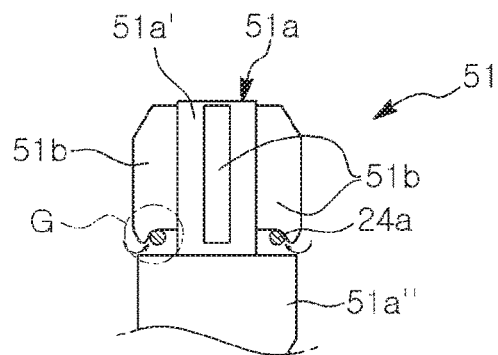
Figure 9A:
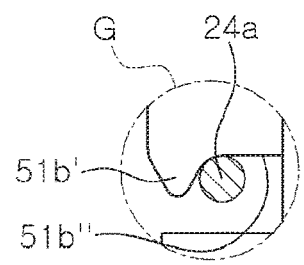
Figure 9C:
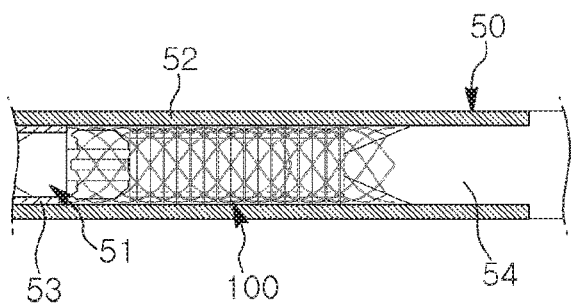
Figure 10A:
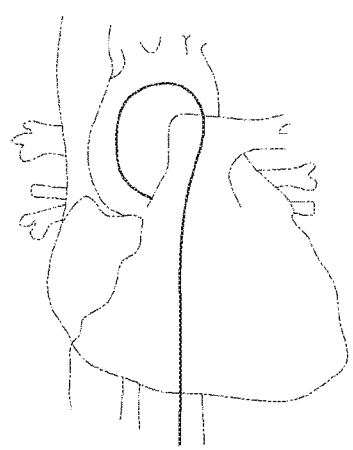
Figure 10B:
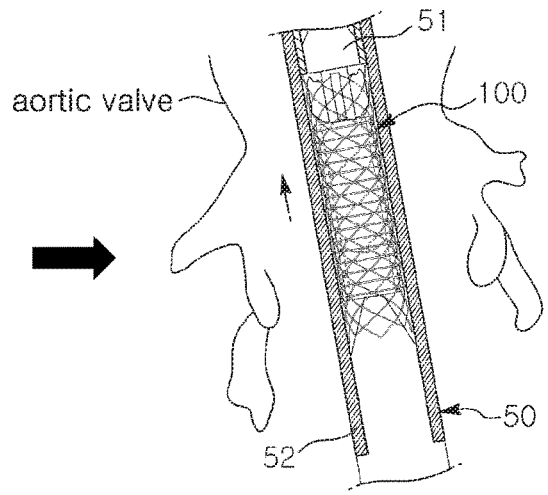
Figure 10D:
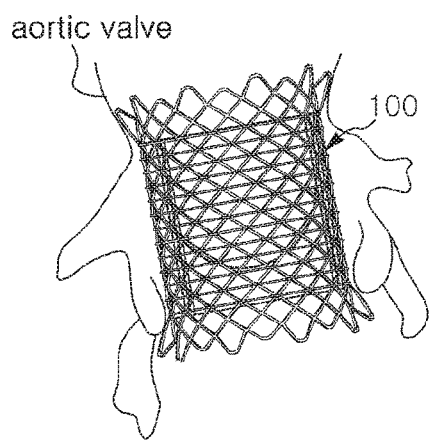
Figure 10C:
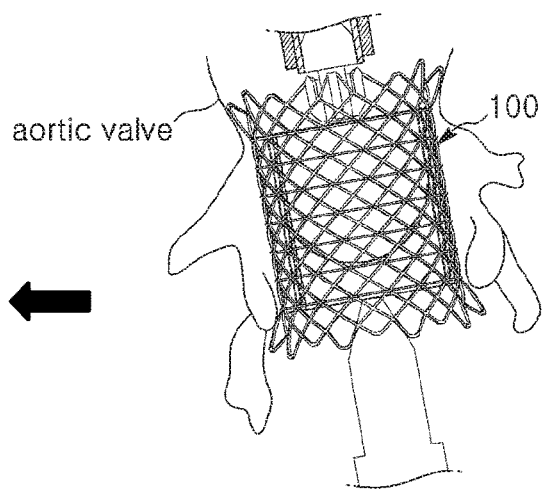

The prosthetic heart valve 100 is compressed by a crimper commonly used to compress a stent, as illustrated in FIGS. 6A and 9C, and after each of the latching folded ends 24a of the valve conduit stent 30 is latched onto the hook portion 51 of a catheter 50, the hook portion 51 is moved to be inserted into the outer tube 52 of the catheter 50, so that the prosthetic heart valve 100 may be used in a surgical procedure on the aortic valve of the heart, as illustrated in FIGS. 7A and 10D, or on the pulmonic valve of the heart, as illustrated in FIGS. 8A and 11D.

Here, the hook portion 51 includes a body 51a, which has one end coupled with the guide tip 54 of the catheter 50 and the other end coupled to an inner tube 53 of the catheter 50, and a multiple number of hook ends 51b, which protrude from one side of the body 51a and which each include a hook 51b' and a mount surface 51b", where the hook 51b' is shaped as an isosceles triangle and has the latching folded ends 24a of the expanding portion 24 latched thereon, while the mount surface 51b" provides a surface on which a latching folded end 24a of the expanding portion 24 latched onto the hook 51b' may be mounted.

Here, the body 51a is composed of a first and a second body segment 51a', 51a" that are detachable from each other. Also, the height of the hook 51b' is formed to such a degree that the latching folded ends 24a are not latched on too deeply.

That is, the first body segment 51a' has multiple hook ends 51b protruding from one side, the hook 51b' is formed on the hook end 51b at a surface close to the surface of the second body segment 51a", the mount surface 51b" is formed between the hook 51b' and the one side of the first body segment 51a', and a narrow space through which the latching folded ends 24a of the expanding portion 24 may move is formed between the hook 51b' and the surface of the second body segment 51a".

Also, the edges of the hooks 51b' are rounded, and the mount surfaces 51b" are formed horizontally.

The effects and advantages of the present invention disclosed above are described below.

As illustrated in FIGS. 1A to 5, the prosthetic heart valve 100 has the first, second, and third connecting threads 1, 2, 3 each sewn in a repeated '∞' form, preventing the valve conduit 10 from being torn by the pressure of the blood flow applied on the valve conduit stent 30.

That is, the valve conduit 10 is secured to the wire stent 20 in a stable manner, so that the durability of the prosthetic heart valve 100 is increased.

Also, the second connecting threads 2 are sewed across the ends of the first connecting threads 1 that are sewn in a semicircular shape with one side open, preventing any tearing that may otherwise occur due to pressure occurring from reverse blood flow at the ends of the first connecting thread 1, i.e. the ends of the valve piece 12a, which are where the greatest pressure is applied during reverse blood flow.

Furthermore, the second connecting threads 2 connect the ends of the heterogeneous tissue pieces 11 by sewing along vertical directions, so that the gaps between the ends of the heterogeneous tissue pieces 11 are made narrower.

Also, the folded portions 14, achieved by folding the ends of the heterogeneous tissue pieces 11, further reduce such gaps.

This prevents blood from flowing between the ends of the heterogeneous tissue pieces 11 and leaking out through the spaces 22 of the wire stent 20.

Since the lengths of the outside tissue pieces 13 are made equal to the length of the cylindrical body 23, the valve conduit 10 may be readily positioned inside the wire stent 20 and may be quickly sewed and connected with the third connecting threads 3.

Here, the folded portions 14 are positioned in 120° intervals as seen in a plan view, allowing the ends of the heterogeneous tissue pieces 11 to be evenly secured on the wire stent 20.

Also, the third connecting threads 3 positioned in predetermined intervals sew across and connect the spaces 22 of the wire stent 20, the outside tissue pieces 13, and the securing pieces 12b along horizontal directions.

That is, the third connecting threads 3 prevent the phenomenon of any one side of the valve conduit 10 being pressed in by the pressure of the blood flow.

In other words, the valve conduit 10 is prevented from having one side pressed in and torn by the pressure of the blood flow.

As illustrated in FIGS. 6A to 9C, the valve conduit stent 30 of the prosthetic heart valve 100 is compressed by a commonly used crimper and is then latched onto the hook portion 51 of the catheter 50, to be inserted into the outer tube 52 of the catheter 50 by a movement of the hook portion 51.

That is, the latching folded ends 24a of the compressed expanding portion 24 are latched onto the hook 51b' of the hook portion 51.

In other words, the latching folded ends 24a are inserted through the narrow space between the hooks 51b' and the second body segment 51a" and mounted on the mount surface 51b" to be thus caught on and secured by the hooks 51b'.

Here, since the hooks 51b' have rounded edges, the latching folded ends 24a may readily move towards the mount surface 51b".

Also, since the mount surface 51b" is formed horizontally, the latching folded ends 24a are not latched on too deeply behind the hooks 51b'.

Thus, one may move the hook portion 51 to insert the valve conduit stent 30 into the outer tube 52 while positioning the valve conduit stent 30 between the inner tube 53 and the guide tip 54 of the catheter 50.

In this manner, the valve conduit stent 30 of the prosthetic heart valve 100 may be used through a catheter 50 in a surgical procedure that includes incising a portion of the chest cavity and operating on the aortic valve or the pulmonic valve of the heart or in a surgical procedure that includes inserting the valve conduit stent 30 along the femoral artery or the femoral vein of the leg and operating on the aortic valve or the pulmonic valve of the heart.

That is, when the prosthetic heart valve 100 is used in a procedure that entails incising a portion of the chest cavity to operate on the aortic valve or pulmonic valve of the heart, as illustrated in FIGS. 6A to 8D, the valve conduit stent 30 is inserted into the outer tube 52 of the catheter 50 with the latching folded ends 24a positioned at the lower part of the valve conduit stent 30, as seen from the front, latched onto the hooks 51b'.

Alternatively, when the prosthetic heart valve 100 is used in a procedure that entails insertion through the femoral artery or the femoral vein of the leg and operating on the aortic valve or the pulmonic valve of the heart, as illustrated in FIGS. 9A to 11D, the valve conduit stent 30 is inserted into the outer tube 52 of the catheter 50 with the latching folded ends 24a positioned at the upper part of the valve conduit stent 30, as seen from the front, latched onto the hooks 51b'.

Thus, the latching folded ends 24a positioned at the upper or lower part of the valve conduit stent 30, as seen from the front, are chosen and latched onto the hooks 51b' to enable the valve pieces 12a to block reverse flow of the blood.

Then, after the outer tube 52 of the catheter 50 is inserted into the aorta or the pulmonary trunk of the heart, the valve conduit stent 30 of the prosthetic heart valve 100 is positioned in the operating position desired by the user, and the outer tube 52 is withdrawn, allowing tight contact with the aortic valve or pulmonic valve of the heart and completing the surgical operation.

Here, the latching folded ends 24a of the valve conduit stent 30 returns from the compressed state to its original state and may be readily removed from the hook portion 51 along the hooks 51b' having rounded edges.

Also, since the latching folded ends 24a of the valve conduit stent 30 are mounted on and not deeply embedded in the horizontally formed mount surface 51b", they can be more readily detached from the hook portion 51.

Since the valve conduit stent 30 of the prosthetic heart valve 100 expands within the narrow lumen of the aortic valve or pulmonic valve of the heart, there is a possibility of cracks occurring in the lumen of the aortic valve or pulmonic valve of the heart. However, the outside tissue pieces 13 formed with a length equal to that of the cylindrical body 23 serve as a protective device.

Figure 12A:
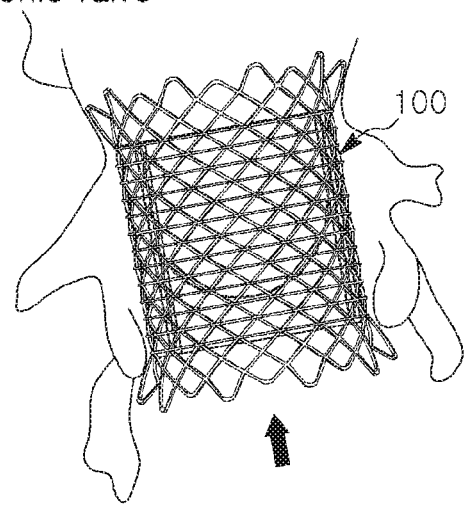
FIGS. 12A, 12B, 13A, and 13B show diagrams illustrating a prosthetic heart valve according to an embodiment of the present invention in use.
Figure 12B:
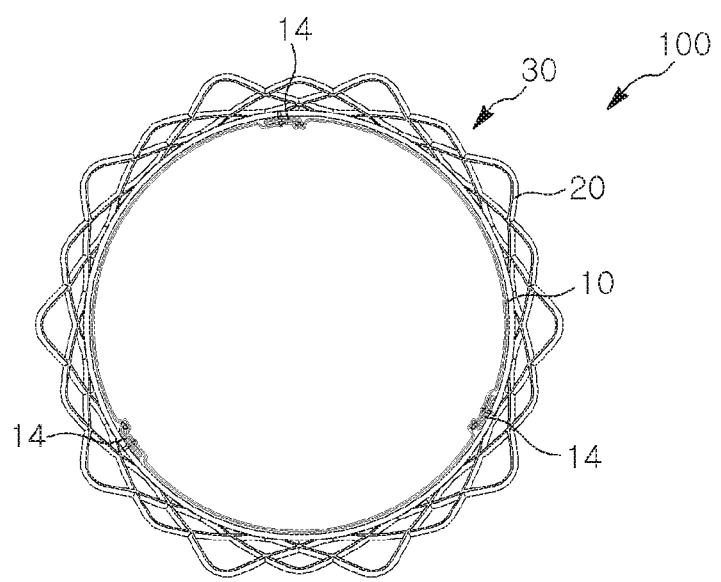

As illustrated in FIGS. 12A and 12B, when blood flows from a lower part to an upper part of the prosthetic heart valve 100, as seen from the front, the valve pieces 12a of the valve conduit 10 that serve as a valve are pushed outwards by the blood flow.

Figure 13A:
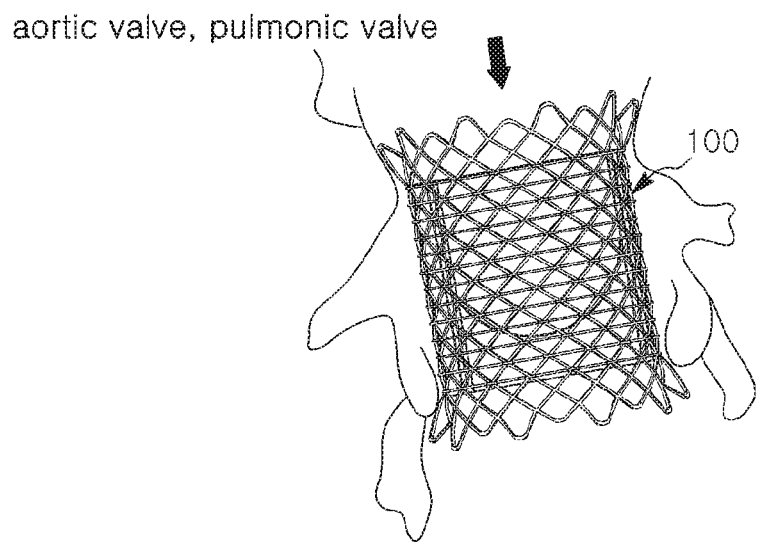
Figure 13B:
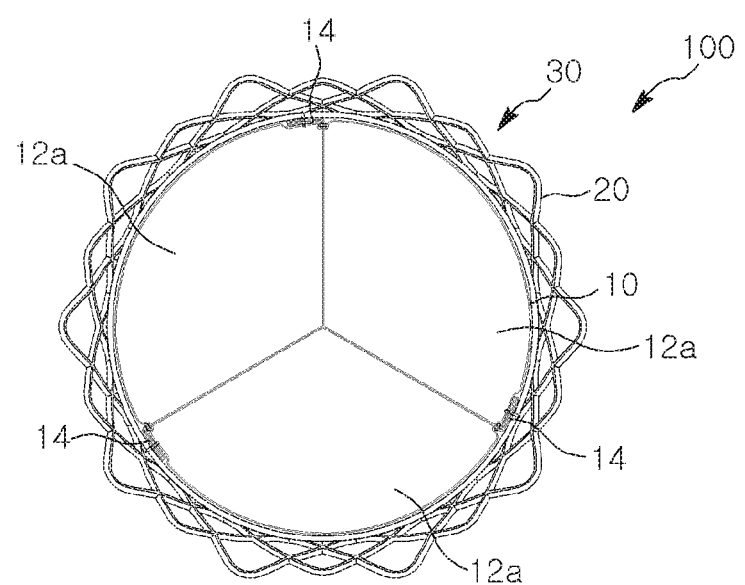

Conversely, when there is reverse flow of the blood, as illustrated in FIGS. 13A and 13B, from the upper part to the lower part of the prosthetic heart valve 100, as seen from the front, the valve pieces 12a of the valve conduit 10 that serve as a valve are pushed inwards by the blood flow.

In this case, the ends of the valve pieces 12a are tightly pushed together, preventing the reverse flow of the blood.

While the foregoing illustrates and describes the present invention using certain preferred embodiments as examples, the present invention is not limited to the embodiments disclosed above. Various modifications and alterations can be made by those having ordinary skill in the field of art to which the present invention pertains without departing from the spirit of the present invention.

DESCRIPTION OF NUMERALS

1: first connecting thread 2: second connecting thread
3: third connecting thread 10: valve conduit
11: heterogeneous tissue piece 12: inside tissue piece
12a,12b: valve piece, securing piece 13: outside tissue piece
14: folded portion 20: wire stent
21: wire 22: space
23: cylindrical body 24: expanding portion
24a: latching folded end 24b: non-latching folded end
30: valve conduit stent 50: catheter
51: hook portion 51a,51b: body, hook end
51b': hook 51b": mount surface
52: outer tube 53: inner tube
54: guide tip 100: prosthetic heart valve

The invention claimed is:

1. A method for manufacturing a prosthetic heart valve using a pericardium, the method comprising:
preparing three heterogeneous tissue pieces, the heterogeneous tissue pieces extracted in a quadrangular shape from a bovine pericardium or a porcine pericardium,
folding each of the heterogeneous tissue pieces to form an inside tissue piece on an inside and an outside tissue piece on an outside, the outside tissue piece having a greater length than the inside tissue piece,
connecting respectively the inside and outside tissue pieces, by sewing with a first connecting thread along a semicircular shape having one side open, such that each of the inside tissue pieces has a valve piece formed on an inside of the first connecting thread and a securing piece formed on an outside of the first connecting thread,
arranging the heterogeneous tissue pieces next to one another to form a cylindrical form, placing both ends of the heterogeneous tissue pieces in contact with one another and exposing outward to connect the heterogeneous tissue pieces by sewing with a second connecting thread along a vertical direction,
folding the heterogeneous tissue pieces at both ends to complete a valve conduit having folded portions,
preparing a wire stent by intertwining wires made of a superelastic shape-memory alloy along a circumferential direction and a lengthwise direction of a cylinder in a network form, the wire stent comprising a cylindrical body having a plurality of spaces formed therein and expanding portions expanding outward from both sides of the cylindrical body,
inserting the valve conduit into an inside of the wire stent and connecting the spaces and the outside tissue pieces and the securing pieces by sewing with a third connecting thread along a horizontal direction to complete a valve conduit stent,
wherein the valve conduit stent is compressed by a commonly used crimper and latched onto a hook portion of a catheter and is inserted into an outer tube of the catheter by a movement of the hook portion.

2. The method for manufacturing a prosthetic heart valve using a pericardium according to claim 1, wherein the first, second, and third connecting threads are sewed repeatedly in a '∞' shape.

3. The method for manufacturing a prosthetic heart valve using a pericardium according to claim 1, wherein the second connecting thread sews across both ends of the first connecting thread.

4. The method for manufacturing a prosthetic heart valve using a pericardium according to claim 1, wherein each of the expanding portions comprises latching folded ends and non-latching folded ends formed in repetition, each of the latching folded ends having a long protruding length and each of the non-latching folded ends having a protruding length shorter than each of the latching folded ends.

5. The method for manufacturing a prosthetic heart valve using a pericardium according to claim 1, wherein a length of the outside tissue piece is formed equal to a length of the cylindrical body.

6. The method for manufacturing a prosthetic heart valve using a pericardium according to claim 1, wherein the hook portion comprises:
- a body having one end thereof coupled with a guide tip of the catheter and the other end thereof coupled to an inner tube of the catheter, and
- a hook end formed protruding from the body, the hook end comprising a hook and a mount surface, the hook shaped as an isosceles triangle and having a latching folded end of the expanding portion latched thereon, the mount surface having the latching folded end of the expanding portion latched onto the hook mounted thereon.

7. The method for manufacturing a prosthetic heart valve using a pericardium according to claim 6, wherein an edge of the hook is rounded, and the mount surface is formed horizontally.

8. A prosthetic heart valve using a pericardium manufactured by the method for manufacturing a prosthetic heart valve according to claim 1.

9. The prosthetic heart valve using a pericardium according to claim 8, wherein the first, second, and third connecting threads are sewed repeatedly in a '∞' shape.

10. The prosthetic heart valve using a pericardium according to claim 8, wherein the second connecting thread sews across both ends of the first connecting thread.

11. The prosthetic heart valve using a pericardium according to claim 8, wherein each of the expanding portion comprises latching folded ends and non-latching folded ends formed in repetition, each of the latching folded ends having a long protruding length and each of the non-latching folded ends having a protruding length shorter than each of the latching folded ends.

12. The prosthetic heart valve using a pericardium according to claim 8, wherein a length of the outside tissue piece is formed equal to a length of the cylindrical body.

13. The prosthetic heart valve using a pericardium according to claim 8, wherein the hook portion comprises:
- a body having one end thereof coupled with a guide tip of the catheter and the other end thereof coupled to an inner tube of the catheter, and
- a hook end formed protruding from the body, the hook end comprising a hook and a mount surface, the hook shaped as an isosceles triangle and having a latching folded end of the expanding portion latched thereon, the mount surface having the latching folded end of the expanding portion latched onto the hook mounted thereon.

14. The prosthetic heart valve using a pericardium according to claim 13, wherein an edge of the hook is rounded, and the mount surface is formed horizontally.

* * * * *